US00PP28846P3

(12) United States Plant Patent
Klemm et al.

(10) Patent No.: US PP28,846 P3
(45) Date of Patent: Jan. 2, 2018

(54) ***PELARGONIUM* PLANT NAMED 'KLEPZ15395'**

(50) Latin Name: *Pelargonium zonale*
Varietal Denomination: KLEPZ15395

(71) Applicant: Klemm+Sohn GmbH & Co. KG, Stuttgart (DE)

(72) Inventors: Nils Klemm, Stuttgart (DE); Martin Glawe, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 80 days.

(21) Appl. No.: 14/998,910

(22) Filed: Mar. 2, 2016

(65) Prior Publication Data

US 2016/0360675 P1 Dec. 8, 2016

(30) Foreign Application Priority Data

Jun. 3, 2015 (CH) ..... 15-3013

(51) Int. Cl.
*A01H 5/02* (2006.01)

(52) U.S. Cl.
USPC ..... Plt./327

(58) Field of Classification Search
USPC ..... Plt./327
See application file for complete search history.

(56) References Cited

PUBLICATIONS

UPOV hit on *Pelargonium* plant named 'KLEPZ 15395', application CH PBR 15-3013, filed Jun. 3, 2015.*
UPOV hit on *Pelargonium* plant named 'KLEPZ15395', application CA PBR 17-9150, filed Mar. 27, 2017.*
UPOV hit on *Pelargonium* plant named 'KLEPZ15395', application QZ PBR 20151524, filed Jul. 1, 2015.*
Select Series Information, 'Moonlight Zonal Geranium', 'KLEPZ15395', downloaded from http://www.selectanorthamerica.com/series_info.aspx?phid=028902331001278 on Jul. 20, 2017.*

* cited by examiner

*Primary Examiner* — Anne M Grunberg
(74) *Attorney, Agent, or Firm* — Bethany R. Roahrig; Barbara Campbell; Cochran Freund & Young, LLC

(57) ABSTRACT

A new *pelargonium* plant particularly distinguished by salmon orange flowers, and an upright growth habit, is disclosed.

1 Drawing Sheet

Genus and species: *Pelargonium zonale.*
Variety denomination: 'KLEPZ15395'.

CROSS-REFERENCE TO RELATED APPLICATIONS

This application claims priority to and the benefit of Switzerland Plant Breeders Rights application filed on Jun. 3, 2015, Application No. 15-3013, the entire contents of which are incorporated herein by reference for all purposes.

An application with the European Community Plant Variety Office was filed on Jul. 1, 2015, File No. 2015-1524.

BACKGROUND OF THE NEW PLANT

The present invention comprises a new and distinct variety of *pelargonium,* botanically known as *Pelargonium zonale* and hereinafter referred to by the variety name 'KLEPZ15395'. 'KLEPZ15395' originated from a cross-combination in June 2010 in Stuttgart, Germany between the female *pelargonium* variety 'PZ-2005-0031' (unpatented) and the proprietary male *pelargonium* variety 'PZ-2002-0037' (unpatented).

Seeds from the cross-combination in June 2010 in Stuttgart, Germany were obtained. The seeds were sown and plants were grown for evaluation. A single plant was selected in June 2011 and subsequently named 'KLEPZ15395'. In September 2011 'KLEPZ15395' was first vegetatively propagated in Stuttgart, Germany by vegetative cuttings from stems. 'KLEPZ15395' was found to reproduce true to type in successive generations of asexual propagation via vegetative cuttings in Stuttgart, Germany.

SUMMARY

The following are the most outstanding and distinguishing characteristics of this new variety when grown under normal horticultural practices in Stuttgart, Germany.

1. Salmon orange flowers; and
2. An upright growth habit.

DESCRIPTION OF THE PHOTOGRAPH

This new *pelargonium* plant is illustrated by the accompanying photograph which shows an overall view of the plant. The photograph is of an approximately ten-week-old plant grown in Stuttgart, Germany under greenhouse conditions in May 2014. The colors shown are as true as can be reasonably obtained by conventional photographic procedures.

DESCRIPTION OF THE NEW VARIETY

The following detailed descriptions set forth the distinctive characteristics of 'KLEPZ15395'. The data which define these characteristics were collected from asexual reproductions carried out in Stuttgart, Germany. Data was collected on plants grown 2 and a half-months after planting in Stuttgart, Germany under greenhouse conditions in June 2015. Color references are to The R.H.S. Colour Chart of The Royal Horticultural Society of London (R.H.S.), 5th edition (2007).

Classification:

*Family.*—Geraniaceae.

*Botanical.*—*Pelargonium zonale.*

*Common.*—*Pelargonium.*

*Designation.*—'KLEPZ15395'.

Parentage:

*Female parent.*—The female *pelargonium* variety 'PZ-2005-0031' (unpatented).

*Male parent.*—The proprietary male *pelargonium* variety 'PZ-2002-0037' (unpatented).

Plant:

*Form.*—Bushy and round.

*Habit.*—Upright.

*Height.*—14.0 cm to 17.0 cm.

*Spread.*—20.0 cm to 21.0 cm.

*Natural flowering season.*—Spring to autumn.

*Propagation type.*—Vegetative cuttings.

*Time to produce a finished flowering plant.*—10 weeks.

*Time to initiate and develop roots.*—18 days.

*Root description.*—White and fine, RHS 155 D.

Stems:

*Quantity of stems per plant.*—4.

*Color.*—RHS 137A.

*Surface texture.*—Sparsely pubescent.

*Stem form.*—Round.

*Diameter.*—0.9 cm.

*Length.*—9.0 cm to 11.0 cm.

*Internode length.*—1.5 cm to 3.0 cm.

*Anthocyanin.*—Present, color is RHS 176B.

Leaves:

*Arrangement.*—Alternate.

*Shape.*—Kidney-shaped.

*Apex.*—Obtuse, round.

*Base.*—Open.

*Margin.*—Crenate.

*Surface texture.*—Upper surface: Rough, sparsely pubescent. Lower surface: Slightly rough to smooth, sparsely pubescent.

*Length.*—4.0 cm to 6.0 cm.

*Width.*—5.0 cm to 7.0 cm.

*Color.*—Upper surface: RHS N137B. Lower surface: RHS 137A.

*Petiole.*—Length: 4.0 cm to 6.0 cm. Diameter: 0.4 cm. Color: RHS 137A and RHS 176C. Strength: Medium.

*Venation pattern.*—Palmate.

*Venation color.*—Upper surface: RHS 137A. Lower surface: RHS 137C.

Inflorescence:

*Lastingness of flowers on the plant.*—6 to 7 days.

*Umbels.*—Quantity of umbels per plant: 4. Length: 5.0 cm to 6.0 cm. Diameter: 8.0 cm to 10 cm.

*Individual florets of the umbel.*—Quantity of florets per umbel: 10 to 12. Depth: 2.2 cm. Diameter: 4.0 cm.

*Fragrance.*—Absent.

Flower buds:

*Cluster shape.*—Round.

*Cluster size.*—Length: 3.5 cm. Width: 3.5 cm.

*Surface texture.*—Rough, sparsely pubescent.

*Bud.*—Height: 1.0 cm to 1.5 cm. Width: 0.5 cm. Shape: Elliptic. Apex: Peaked. Base: Blunt. Margin: Entire. Color: RHS 137B.

Petals:

*Quantity per flower.*—6 to 7 and petaloids.

*Shape.*—Drop-shaped.

*Apex.*—Round.

*Base.*—Attenuate.

*Margin.*—Entire.

*Length.*—2.0 cm.

*Width.*—1.5 cm.

*Surface texture.*—Upper surface: Smooth. Lower surface: Smooth.

*Color of lobes.*—Upper lobes: Upper surface: RHS 33A. Lower surface: RHS 32A. Lower lobes: Upper surface: RHS 33A. Lower surface: RHS 32A.

Petaloids:

*Quantity per flower.*—3 to 4.

*Shape.*—Moderate.

*Apex.*—Round.

*Base.*—Attenuate.

*Margin.*—Obtuse, blunt.

*Texture* (*upper and lower surfaces*).—Smooth.

*Length.*—0.2 cm to 0.8 cm.

*Width.*—0.1 cm to 0.5 cm.

*Color.*—Upper surface: RHS 33A. Lower surface: RHS 32A.

Sepals:

*Number per flower.*—5.

*Shape.*—Elliptic.

*Apex.*—Peaked.

*Base.*—Obtuse.

*Margin.*—Entire.

*Surface texture.*—Upper surface: Smooth. Lower surface: Sparsely pubescent.

*Color.*—Upper surface: RHS 138B and RHS 176C. Lower surface: RHS 138B and RHS 176C.

*Length.*—0.9 cm.

*Width.*—0.3 cm.

Pedicel:

*Length.*—1.0 cm to 1.5 cm.

*Diameter.*—0.1 cm.

*Color.*—RHS 176B.

*Surface texture.*—Sparsely pubescent.

*Strength.*—Medium.

Peduncle:

*Length.*—10.0 cm to 13.0 cm.

*Diameter.*—0.4 cm to 0.5 cm.

*Color.*—RHS 176A.

*Surface texture.*—Rough, sparsely pubescent.

*Strength.*—Medium to strong.

Reproductive organs:

*Stamens.*—Quantity of stamens per flower: 1 to 5, maximum. Anther length: 0.15 cm. Filament length: 0.8 cm. Filament color: RHS 49D. Pollen amount: Moderate. Pollen color: RHS 26A.

*Pistils.*—Number: 1. Stigma color: RHS 60D. Style length: 0.5 cm. Style color: RHS 60A. Ovary arrangement: Central. Ovary color: RHS 145C. Ovary diameter: 0.2 cm. Ovary length: 0.4 cm.

Fruit and seed set: None observed.
Disease and pest/insect resistance: None observed.

COMPARISON WITH PARENTAL LINES AND KNOWN VARIETY

'KLEPZ15395' is distinguished from its parents as described in Table 1:

TABLE 1

Comparison with Parental Lines

| Characteristic | 'KLEPZ15395' | Female parent 'PZ-2005-0031' | Male Parent 'PZ-2002-0037' |
|---|---|---|---|
| Flower color | Salmon orange | Dark red | Orange |
| Growth | Medium | Strong | Compact |
| Production | Good | Medium | Medium |

'KLEPZ15395' can be compared to the commercial variety MOONLIGHT 'Guido' (unpatented). Differences between the two varieties are described in Table 2:

TABLE 2

Comparison with Similar Variety

| Characteristic | 'KLEPZ15395' | Commercial line MOONLIGHT 'Guido' |
|---|---|---|
| Production | Good | Medium |
| Earliness | Early | Medium early |

We claim:

1. A new and distinct variety of *pelargonium* plant named 'KLEPZ15395' as illustrated and described herein.

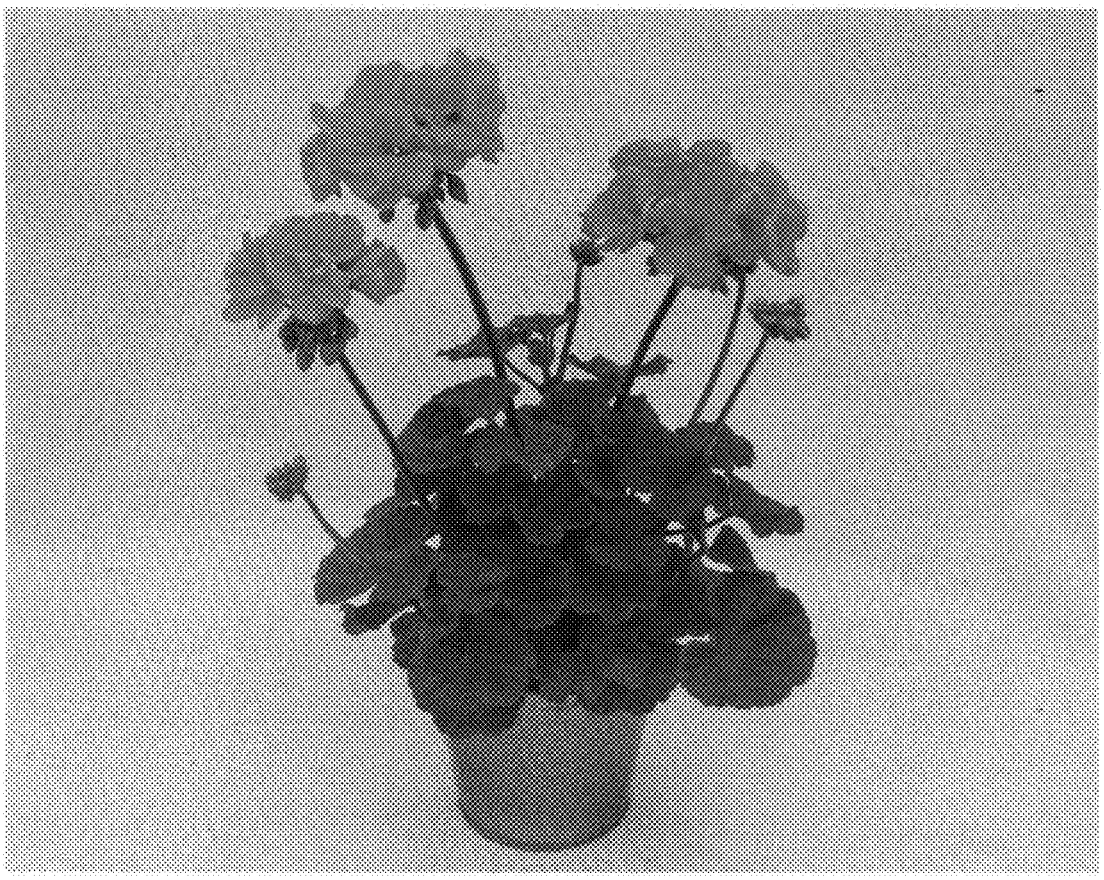

* * * * *